United States Patent
Gumbrecht et al.

(10) Patent No.: US 9,777,323 B2
(45) Date of Patent: Oct. 3, 2017

(54) ASSEMBLY AND METHOD FOR ANALYZING NUCLEIC ACID SEQUENCES BY WAY OF SO-CALLED SEQUENCING-BY-SYNTHESIS

(71) Applicant: Siemens Aktiengesellschaft, Munich (DE)

(72) Inventors: Walter Gumbrecht, Herzogenaurach (DE); Oliver Hayden, Herzogenaurach (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 415 days.

(21) Appl. No.: 14/404,964

(22) PCT Filed: Jun. 13, 2013

(86) PCT No.: PCT/EP2013/062209
§ 371 (c)(1),
(2) Date: Dec. 2, 2014

(87) PCT Pub. No.: WO2013/189818
PCT Pub. Date: Dec. 27, 2013

(65) Prior Publication Data
US 2015/0126375 A1    May 7, 2015

(30) Foreign Application Priority Data
Jun. 18, 2012   (DE) .................. 10 2012 210 183

(51) Int. Cl.
*C12Q 1/68*       (2006.01)
*G01N 27/414*   (2006.01)

(52) U.S. Cl.
CPC ......... *C12Q 1/6874* (2013.01); *C12Q 1/6869* (2013.01); *G01N 27/4145* (2013.01)

(58) Field of Classification Search
USPC ......................................... 435/91.1
See application file for complete search history.

(56) References Cited

U.S. PATENT DOCUMENTS

| 5,296,122 A | 3/1994 | Katsube et al. |
| 7,595,883 B1 | 9/2009 | El Gamal et al. |
| (Continued) | | |

FOREIGN PATENT DOCUMENTS

| CN | 1944682 A | 4/2007 |
| CN | 101669026 A | 3/2010 |
| (Continued) | | |

OTHER PUBLICATIONS

International Search Report PCT/ISA/210 for International Application No. PCT/EP2013/062209 dated Oct. 1, 2013.
(Continued)

*Primary Examiner* — Kenneth Horlick
(74) *Attorney, Agent, or Firm* — Harness, Dickey & Pierce, P.L.C.

(57) ABSTRACT

An assembly and a method are disclosed for analyzing nucleic acid sequences by way of so-called sequencing-by-synthesis. According to an embodiment of the invention, a chemical substance group that is released when a nucleotide bonds to a nucleic acid sequence to be sequenced is detected. The reagents are applied by way of a spraying device to a sensor that detects the released substance group. This has the advantage that no lateral flow occurs. The rate of false-negative and false-positive results is significantly reduced. Furthermore, a small amount of the reagent is sufficient to completely wet the sensor. Filling of the supply and discharge lines as for a flow cell is not necessary.

19 Claims, 3 Drawing Sheets

(56) References Cited

U.S. PATENT DOCUMENTS

| | | |
|---|---|---|
| 8,470,164 B2 | 6/2013 | Rothberg et al. |
| 2002/0012930 A1 | 1/2002 | Rothberg et al. |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2007/0092872 A1 | 4/2007 | Rothberg et al. |
| 2007/0155037 A1 | 7/2007 | Chou |
| 2007/0166729 A1 | 7/2007 | Kambara et al. |
| 2009/0026082 A1 | 1/2009 | Rothberg et al. |
| 2009/0075838 A1 | 3/2009 | El Gamal et al. |
| 2009/0084979 A1* | 4/2009 | DeWalch ............ G01N 21/645 250/458.1 |
| 2009/0197326 A1 | 8/2009 | El Gamal et al. |
| 2010/0034445 A1 | 2/2010 | Ulmer |
| 2010/0261595 A1* | 10/2010 | Schaefer ................. B01L 9/06 494/20 |
| 2010/0308843 A1 | 12/2010 | Coppe et al. |
| 2011/0172127 A1 | 7/2011 | Jacobson et al. |
| 2011/0241081 A1 | 10/2011 | Rothberg et al. |
| 2013/0078623 A1 | 3/2013 | El Gamal et al. |
| 2013/0324421 A1 | 12/2013 | Rothberg et al. |
| 2015/0126378 A1 | 5/2015 | Rothberg et al. |

FOREIGN PATENT DOCUMENTS

| | | |
|---|---|---|
| CN | 102203282 A | 9/2011 |
| DE | 29923907 U1 | 7/2001 |
| WO | WO 2009064166 A2 | 5/2009 |

OTHER PUBLICATIONS

Written Opinion of the International Searching Authority PCT/ISA/237 for International Application No. PCT/EP2013/062209 dated Oct. 1, 2013.
Chinese Office Action and English translation thereof dated Sep. 6, 2015.
German Office Action dated Feb. 23, 2016.

* cited by examiner

ASSEMBLY AND METHOD FOR ANALYZING NUCLEIC ACID SEQUENCES BY WAY OF SO-CALLED SEQUENCING-BY-SYNTHESIS

PRIORITY STATEMENT

This application is the national phase under 35 U.S.C. §371 of PCT International Application No. PCT/EP2013/062209 which has an International filing date of Jun. 13, 2013, which designated the United States of America, and which claims priority to German patent application number DE 102012210183.7 filed Jun. 18, 2012, the entire contents of each of which are hereby incorporated herein by reference.

FIELD

At least one embodiment of the invention generally relates to an assembly and a method for analyzing nucleic acid sequences by way of so-called sequencing-by-synthesis.

BACKGROUND

In the field of "next generation sequencing", two main aims are pursued. Firstly, the analysis duration is to be significantly shortened. This should enable an analysis of the human genome for a price of under US$1000. Secondly, the quality of the data obtained is to be maintained or even further improved with rapid analysis times.

The NGS methods include sequencing-by-synthesis, for example, pyrosequencing and "ion semiconductor sequencing".

Pyrosequencing is based on the inclusion of nucleotides in a DNA strand. The DNA to be sequenced is provided as a single strand bound to microspheres (or "microbeads") and serves as a template. The addition of the four types of nucleotides is carried out one after another. When a nucleotide matching the template is added, pyrophosphate is released by way of the DNA polymerase. This leads to a flash of light triggered by the enzyme cascade, which is optically detected. In order to enable a parallel analysis, the microspheres are arranged in micro-depressions or "microwells" in an array. The optical signal of individual wells is then analyzed.

Ion semiconductor sequencing is also based on the inclusion of nucleotides. The successful inclusion of a nucleotide in the DNA matrix strand is indicated by the release of protons. For this purpose, in particular, a measurement of the pH value is carried out with chemically sensitive field effect transistors (chemFETs), also known as ion-selective field effect transistors (ISFETs).

US 2009/0026082 A1 combines both these methods. In this process, microspheres are arranged with DNA single strands in depressions. The installation of the respective nucleotide is detected with the aid of the pH value, measured by way of a chemFET.

The sequencing techniques mentioned require a large number of different reagents which are fed to the respective analysis unit one after another. These include, in particular, the reagents which comprise one of the four types of nucleotide or nucleoside triphosphate (NTP). The feeding in of the reagents typically takes place in flow cells. The lateral flow of the reagents over the sensor array which occurs herein is disadvantageous for the detection of the pyrophosphate substance group or the released protons. These substances can flow in the direction of flow from a first depression to a second depression and lead there to false positive results. Furthermore, a reduced concentration of the test components is produced in the first depression, due to the lateral flow, which leads to false negative results. The diffusion of the protons away from the chemFET also leads to very low pH value changes and can disadvantageously lead to false negative results. Furthermore, due to the very small measuring effects, disadvantageously, an insufficient resolution of the homopolymers is produced. What is designated homopolymers herein is the attachment together of several nucleotides of the same type.

A further disadvantage of the sequencing techniques mentioned is the high usage of reagents. This is due to the fact that the entire volume of the flow cell including all the supply and discharge lines must be filled with each new reagent. Furthermore, the thickness of the fluid layer over the array must be ca. 100 µm in order to enable the supply of all the depressions of the array with the new reagent.

SUMMARY

Embodiments of the invention are directed to an assembly and a method for analyzing nucleic acid sequences.

An assembly and a method are disclosed. The dependent claims relate to advantageous developments of the invention.

The assembly according to an embodiment of the invention is designed for analyzing nucleic acid sequences by way of so-called sequencing-by-synthesis. In the sequencing of nucleic acid sequences by synthesis, a chemical substance group which is released during binding of a nucleotide to a nucleic acid sequence to be sequenced is detected. For this purpose, the assembly comprises a sensor for detection of the released substance group. Finally, the assembly comprises a spraying device for applying reagent to this sensor.

In the method according to an embodiment of the invention for analyzing nucleic acid sequences by way of sequencing-by-synthesis, at least one reagent is applied to the sensor. The application takes place in such a manner that the reagent is sprayed onto the sensor.

BRIEF DESCRIPTION OF THE DRAWINGS

The invention will now be described in greater detail by reference to example embodiments which are illustrated in the drawings.

DETAILED DESCRIPTION OF THE EXAMPLE EMBODIMENTS

Figure 1:
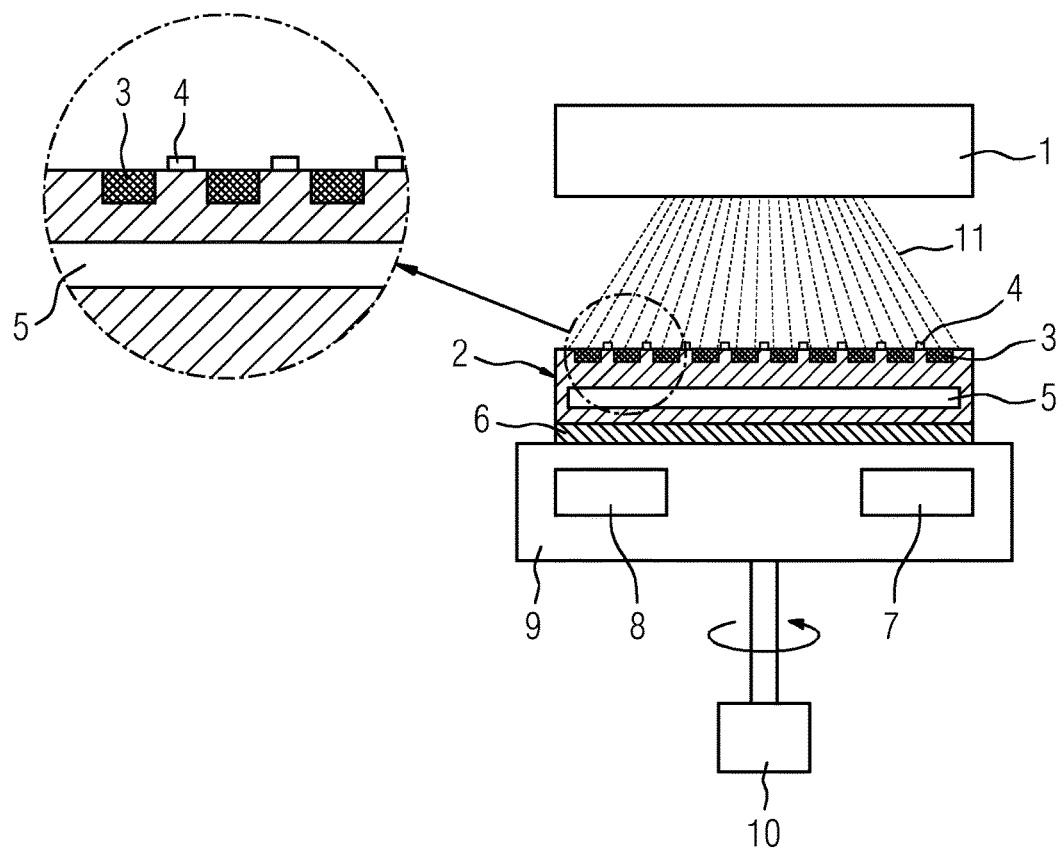
FIG. 1 shows a schematic view of an assembly for analyzing nucleic acid sequences with ISFET sensors and reference electrodes.

An assembly and a method are disclosed. The dependent claims relate to advantageous developments of the invention.

The assembly according to an embodiment of the invention is designed for analyzing nucleic acid sequences by way of so-called sequencing-by-synthesis. In the sequencing of nucleic acid sequences by synthesis, a chemical substance group which is released during binding of a nucleotide to a nucleic acid sequence to be sequenced is detected. For this purpose, the assembly comprises a sensor for detection of the released substance group. Finally, the assembly comprises a spraying device for applying reagent to this sensor.

In the method according to an embodiment of the invention for analyzing nucleic acid sequences by way of sequencing-by-synthesis, at least one reagent is applied to the sensor. The application takes place in such a manner that the reagent is sprayed onto the sensor.

In this assembly and this method of at least one embodiment, advantageously no lateral flow takes place. Therefore, advantageously, false negative and false positive results are reduced. Also, greater measuring effects are achieved, so that the analysis of the homopolymers is improved. Furthermore, a small quantity of the reagent is sufficient to wet the sensor completely. A preferred thickness of the fluid layer of the reagent on the sensor is 1 µm. Furthermore, filling of the supply and discharge lines, as in the case of a flow cell, is not needed. This also advantageously reduces the usage of reagents.

In an advantageous development and configuration of an embodiment of the invention, the assembly comprises a sensor mount which is configured rotatable relative to the spraying device.

The sensor is firmly attached to the sensor mount. Advantageously, even wetting of the sensor by rotation of the sensor mount is achieved. Furthermore, excess reagent, in particular a washing fluid, can be carried by high rotation speeds to the outer edge of the sensor mount. Preferably, the sensor mount is not, or is only slowly, rotated during the application of a nucleotide-containing reagent. By this means, a lateral flow is advantageously prevented. Advantageously, electronics which accept the electrical sensor signals from the sensor and passes them on to an external measurement value recording system can be built into the sensor mount.

The sensor is suitably integrated into a chip.

In a further advantageous embodiment and development of the invention, the sensor is an ion-selective field effect transistor (ISFET). By this, released protons can be detected during the synthesis. Nucleic acid sequences to be sequenced are applied onto the ISFET together with a primer before the analysis. Furthermore, an enzyme for nucleic acid synthesis is added to the nucleic acid sequence to be sequenced. In the case of a DNA as the nucleic acid sequence, for example, a DNA polymerase is added. In the case of other nucleic acid sequences, the corresponding enzyme to be synthesized is added. Alternatively or additionally, a sensor can be used which measures a chemiluminescence light signal. Preferably, said sensor measures the light signal, which is generated by way of an enzyme cascade based on the release of a pyrophosphate.

In a further advantageous embodiment and development of the invention, the assembly comprises two sensors. Advantageously, a plurality of measurements can thus be made simultaneously, so that a rapid, parallel determination of many sequences can be carried out. Spraying of the reagents advantageously takes place for both sensors simultaneously in one operation. The sensors are preferably arranged in a sensor array.

In a further advantageous embodiment and development of the invention, a hydrophobic boundary layer is arranged between two sensors in each case. This hydrophobic boundary layer serves as compartmentalization for the reagents on the sensors. Running together of the reagents of the adjacently arranged sensors is therefore advantageously prevented. It is also advantageously prevented that the nucleic acids to be sequenced are arranged in microwells.

In a further advantageous embodiment and development of the invention, the hydrophobic boundary layer comprises a metal, in particular gold.

In a further advantageous embodiment and development of the invention, the hydrophobic boundary layer represents a reference electrode for the ion-selective field effect transistor. Advantageously, the reference electrode is then arranged spatially close to the sensor. Consequently, only a small electrical resistance arises between the sensor and the reference electrode, so that noise in the signal is advantageously reduced.

In a further advantageous embodiment and development of the invention, the spraying device is an ultrasonic atomizer. Advantageously, droplet sizes of less than 1 µm can thus be achieved.

In a further advantageous embodiment and development of the invention, the reagent is a nucleotide-containing solution, a washing fluid or a protection fluid. Advantageously, in the method for analyzing nucleic acid sequences, firstly a nucleotide-containing solution, in particular a dNTP solution, is applied to the sensor. This solution contains only a single type of nucleotide. During the application of the nucleotide-containing solution, the sensor mount can rotate slowly. The nucleotide solution is advantageously applied in such a way that, on each sensor a fluid volume forms which is locally separate from its neighboring sensors and which forms an electrochemical contact between the sensor and the edge of the reference electrode.

If the nucleotide is included in the nucleic acid sequence to be sequenced, then protons are produced. These protons generate a signal only in the respective sensor. Carry-over of the protons from a first sensor to a second sensor is advantageously prevented.

Following reception of the signal, the rotation speed is preferably significantly increased and the washing fluid, typically in a larger volume than the nucleotide solution is sprayed onto the sensor and spun off. The washing fluid is typically of a type such that it entirely removes the nucleotides present in the first solution. The sensor mount is rotated until the washing fluid has almost entirely dried.

Subsequently, a further nucleotide-containing solution is sprayed onto the sensor as a reagent. Only one type of nucleotide is contained in this nucleotide-containing solution also. Subsequently, the nucleotide-containing solution is again removed by way of a washing fluid.

Alternatively, the sensors can be provided with a protection fluid. This fluid comprises a water-soluble film-forming agent, which advantageously prevents the lateral diffusion of the released substance group during the sequencing.

In a further advantageous embodiment and development of the invention, the reagent is sprayed onto the sensor as an aerosol.

FIG. 1 shows schematically an assembly for nucleic acid synthesis. This comprises an ultrasonic atomizer 1, a microarray chip 2, a sensor mount 9 and an electric motor 10 for rotation. The microarray chip 2 comprises ion-selective field effect transistors (ISFETs) 3, reference electrodes 4 and a signal processing unit 5. The microarray chip 2 is fixed with a first device 6 for fixing to the sensor mount 9. This first device is preferably a clamping device. Alternatively, the microarray chip 2 can be fastened to the sensor mount 9 by way of negative pressure. The area of an array is typically 1 cm2, wherein an array preferably comprises up to 1,000,000 sensors. The sensor mount 9 comprises a power supply 8 and a data processing unit 7 for the ISFETs 3.

A first reagent 11 is sprayed onto the microarray chip 2 by way of the ultrasonic atomizer 1. The first reagent is typically a washing fluid. Due to the use of relatively large volumes of the washing fluid, this can alternatively be sprayed from nozzles in the form of a jet. While the first reagent 11 is sprayed onto the microarray chip 2, the electric motor 10 rotates. Due to the rotation, the first reagent 11 is evenly distributed over the microarray chip 2. A subsequent increase in the rotation speed leads thereto that the first reagent 11 is flung off radially. Through a variation of the rotation speed, defined drying states can be set.

Figure 2:
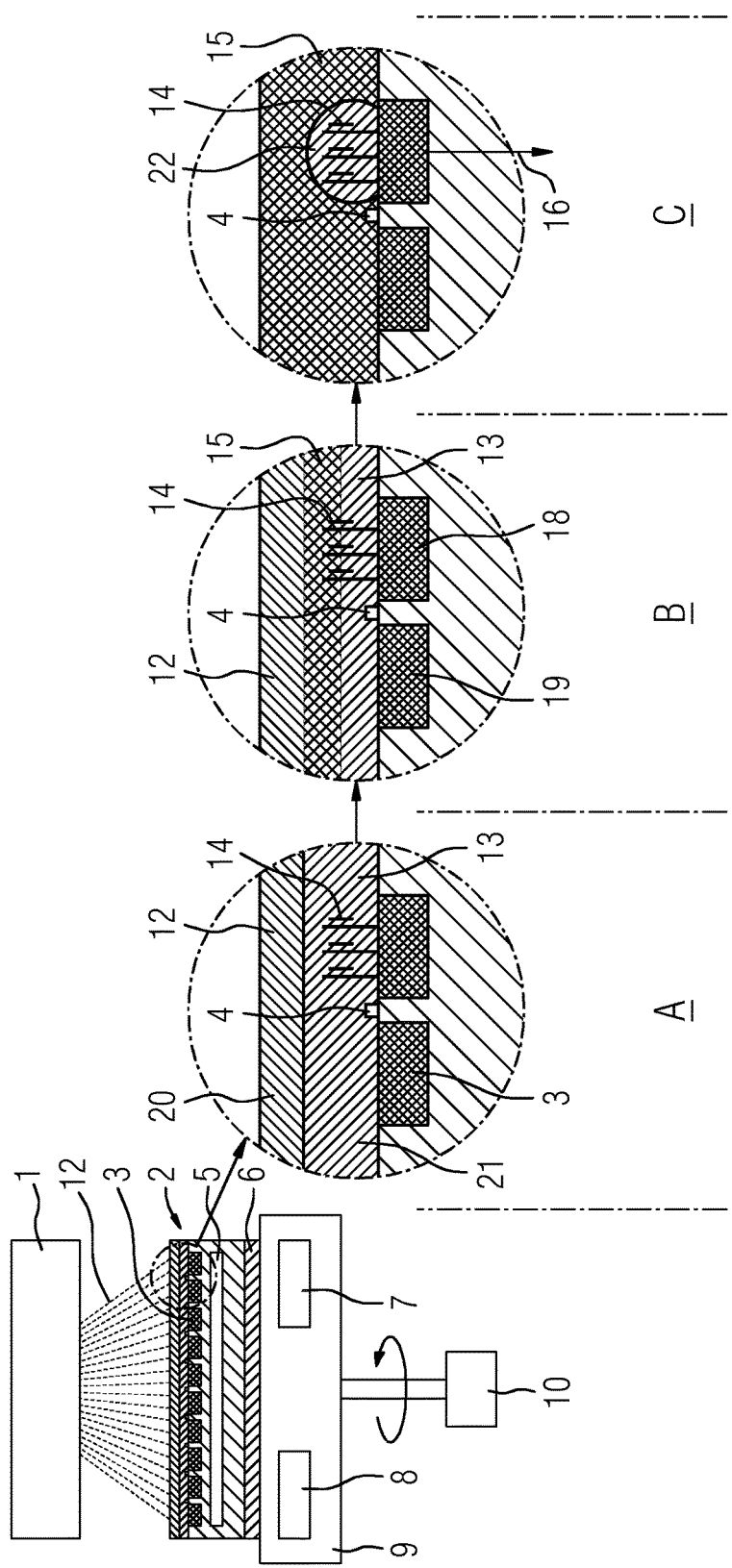
FIG. 2 shows schematically a method for analyzing nucleic acid sequences.

FIG. 2 shows schematically a method for operating an assembly for analyzing nucleic acid sequences. The assembly corresponds to the arrangement set out in FIG. 1. The microarray chip 2 further comprises active ISFETs 18 and passive ISFETs 19. Active ISFETs 18 comprise the DNA sequence 14 with a primer for DNA synthesis. Furthermore, a DNA polymerase is bound to the DNA sequence 14 that is to be investigated. The microarray chip 2 preferably comprises active ISFETs 18.

Following cleaning of the microarray chip 2 with a first reagent 11 and subsequent drying of the microarray chip 2, in a next step, a second reagent 13, a protection fluid, is applied to the microarray chip 2. A typical protection fluid is a wash buffer with a substance which increases the viscosity, in particular a film-forming agent such as polyvinylpyrrolidone. The rotation speed of the electric motor 10 is set such that a first layer 21 with the second reagent 13 preferably has a thickness of 1 μm.

A third reagent 12 is applied on this first layer 21 with the second reagent 13, as shown in section A. The third reagent 12 comprises a first nucleotide type (typically adenine, thymine, cytosine or guanine, in each case as deoxyribonucleoside triphosphates (dNTP)). Herein, the third reagent 12 falls finely distributed essentially vertically onto the first layer 21. The rotation speed of the electric motor 10 is set such that a second layer 20 with the third reagent 12 preferably has a thickness of 1 μm.

The rotation speed of the electric motor 10 is decelerated after application of the third reagent 12. The third reagent 12 diffuses evenly into the first layer 21 perpendicularly to the layer plane. A mixed layer 15 forms from the second and third reagent 12, 13. This is shown in section B of FIG. 2.

The nucleotides of the third reagent 12 can become attached to the DNA sequence 14 to be investigated. This is shown in section C of FIG. 2. Through the attachment of the nucleotides which fit to the primer 14, protons are released. The concentration thereof can be measured with the aid of the ISFET sensors. The measurement variable is the pH value. Due to the lateral diffusion restricted by the film-forming agent, carry-over of the protons released is largely prevented. On successful attachment of a nucleotide to the primer 14, a signal 16 is produced.

Following signal processing, the rotation speed is significantly increased and washing fluid is again applied as the first reagent 11. The microarray chip 2 is thus cleaned of fluids and reagents. Alternatively, moist air is sprayed by way of the ultrasonic atomizer 1 to clean the sensor.

In a next step, a second reagent 13 is applied as a protection fluid and a third reagent 12 with a second nucleotide type is applied. Due to the vertical application of the fluids and the associated prevention of lateral diffusion, no carry-over takes place.

Figure 3:
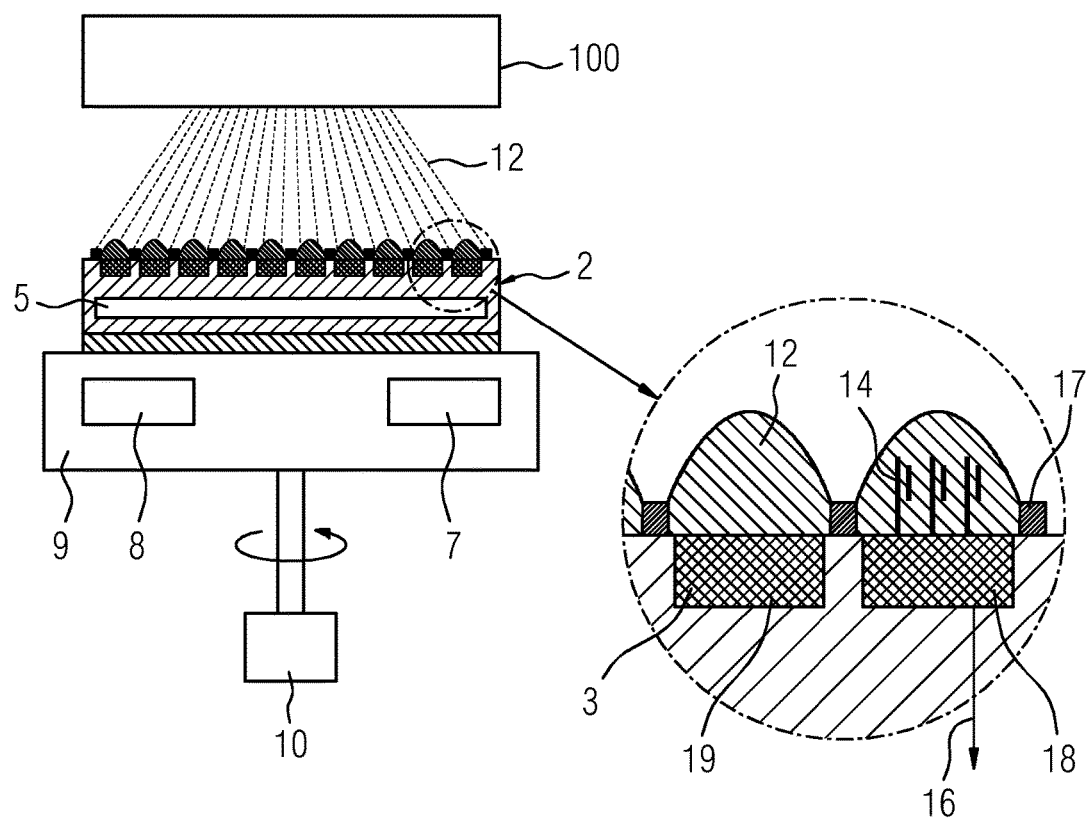
FIG. 3 shows schematically an assembly for analyzing nucleic acid sequences with ISFET sensors and hydrophobic boundary structures as reference electrodes.

FIG. 3 shows a schematic view of an alternative assembly for analyzing nucleic acid sequences. This assembly comprises a nozzle device 100 for atomizing the reagent, a microarray chip 2 and an electric motor 10 for rotation, a signal processing unit 5, a power supply 8 and a data processing unit 7. The microarray chip 2 comprises field effect transistors 3. The ISFETs 3 are each separated from one another by way of a hydrophobic boundary layer 17. This hydrophobic boundary layer 17 comprises gold. It therefore serves as a reference electrode for the respective ISFET 3. The microarray chip 2 further comprises active ISFETs 18 and passive ISFETs 19. A third reagent 12 with nucleotides is atomized onto the microarray chip 2. The third reagent is distributed on the microarray chip 2 by way of slow rotation of the sensor mount 9. The hydrophobic boundary layer 17 prevents flowing together of the third reagent 12 on a plurality of ISFETs. Droplets with a size of approximately 1 μm$^3$ form.

On successful inclusion of a nucleotide of the third reagent 12 into the DNA 14 to be investigated, a signal 16 is generated by way of the released proton. Following successful processing of the signal 16, the first reagent 11 is sprayed onto the microarray chip 2 as the washing fluid. Due to the fast rotation speed, the microarray chip 2 is cleaned of the third reagent 3. Following completion of the cleaning, which is ascertained by way of a pH signal, a fourth reagent with a further nucleotide type is sprayed on. In this way, rapid process execution based on short spraying-on times in the range of seconds is possible.

The invention claimed is:

1. An assembly for analyzing nucleic acid sequences via so-called sequencing-by-synthesis, wherein a chemical substance group released during binding of a nucleotide to a nucleic acid sequence to be sequenced is detectable, the assembly comprising:
   at least two sensors to detect the released substance group; and
   a spraying device to apply reagents onto the sensors, wherein a hydrophobic boundary layer is arranged between the at least two sensors.

2. The assembly of claim 1, further comprising:
   a sensor mount, configured rotatable relative to the spraying device.

3. The assembly of claim 1, wherein the at least two sensors are integrated into a chip.

4. The assembly of claim 1, wherein the at least two sensors are ion-selective field effect transistors (ISFET).

5. The assembly of claim 1, wherein the hydrophobic boundary layer comprises a metal.

6. The assembly of claim 1, wherein the hydrophobic boundary layer is a reference electrode of an ion-selective field effect transistor (ISFET).

7. The assembly of claim 1, wherein the spraying device is an ultrasonic atomizer.

8. A method for analyzing nucleic acid sequences via so-called sequencing-by-synthesis, the method comprising:
   spraying at least one reagent to the onto at least two sensors configured to detect a substance group released during binding of a nucleotide to a nucleic acid sequence; and
   arranging a hydrophobic boundary layer between the at least two sensors.

9. The method as claimed in claim 8, wherein the reagent is a nucleotide-containing solution, a washing fluid or a protection fluid.

10. The method of claim 8, further comprising:
    rotating a die sensor mount relative to a spraying device useable to spray the at least one reagent.

11. The method of claim 8, wherein the at least one reagent is sprayed onto the at least two sensors as an aerosol.

12. The assembly of claim 2, wherein the at least two sensors are integrated into a chip.

13. The assembly of claim 2, wherein the at least two sensors are ion-selective field effect transistors (ISFET).

14. The assembly of claim 5, wherein the metal is gold.

15. The assembly of claim 5, wherein the hydrophobic boundary layer is a reference electrode of an ion-selective field effect transistor (ISFET).

16. The method of claim 9, further comprising:
  rotating a die sensor mount relative to a spraying device useable to spray the at least one reagent.

17. The method of claim 9, wherein the at least one reagent is sprayed onto the at least two sensors as an aerosol.

18. The method of claim 10, wherein the at least one reagent is sprayed onto the at least two sensors as an aerosol.

19. The method of claim 16, wherein the at least one reagent is sprayed onto the at least two sensors as an aerosol.

\* \* \* \* \*